United States Patent [19]

Lerman

[11] Patent Number: 4,574,810
[45] Date of Patent: Mar. 11, 1986

[54] AUTOMATIC THRESHOLD DEFIBRILLATOR

[76] Inventor: Bruce B. Lerman, 112 Turtle Creek Rd., Apt. #9, Charlottesville, Va. 22901

[21] Appl. No.: 657,949

[22] Filed: Oct. 5, 1984

[51] Int. Cl.$^4$ ............................ A61B 5/05; A61N 1/36
[52] U.S. Cl. ................... 128/419 D; 128/734
[58] Field of Search ........................... 128/734, 419 D

[56] References Cited

U.S. PATENT DOCUMENTS

| 3,556,083 | 1/1971 | Grichnik et al. | 128/734 |
|---|---|---|---|
| 3,747,605 | 7/1973 | Cook | 128/419 D |
| 3,860,009 | 1/1975 | Bell et al. | 128/419 D |
| 3,862,636 | 1/1975 | Bell et al. | 128/419 D |
| 4,303,075 | 12/1981 | Heilman et al. | 128/419 D |
| 4,328,808 | 5/1982 | Charbonnier et al. | 128/419 D |

OTHER PUBLICATIONS

Machin, "Thoracic Impedance of Human Subjects", *Med. & Biol. Eng. & Comput.*, Mar. 1978, vol. 16, No. 2, pp. 169-178.

MacPherson et al., "Integrated Circuit Measurement of Skin Conductance", *Behaviour Research Methods and Instrumentation*, Aug. 1976, vol. 8, No. 4, pp. 361-364.

*Primary Examiner*—William E. Kamm
*Assistant Examiner*—Mitchell J. Shein
*Attorney, Agent, or Firm*—Fidelman, Wolffe & Waldron

[57] ABSTRACT

A defibrillator which will automatically ascertain the transthoracic resistance of the patient and then automatically apply a defibrillation shock according to the transthoracic resistance and an amperes per ohm factor.

11 Claims, 2 Drawing Figures

AUTOMATIC THRESHOLD DEFIBRILLATOR

BACKGROUND OF THE INVENTION

Widespread use of DC defibrillators in patients suffering cardiac arrest has greatly increased the rate of successful resuscitation both in and out of hospitals over the past few decades. Defibrillation is applicable to life-threatening cardiac arrests resulting from ventricular fibrillation which occurs because of asynchronous depolarization of cardiac cells. When sufficient electrical energy is delivered to the heart from an external defibrillator through a set of paddles (electrodes), all cardiac cells briefly arrest and thereafter synchronous or normal depolarization may once again resume.

The defibrillator equipment presently offered to the medical arts (stores) discharges the electrical energy through an RLC circuit which is manually triggered by the physician. The heretofore standard quantity of the electrical pulse to be delivered has been calibrated in terms of joules of energy. The many studies reported in the medical literature of attempts to determine the optimal electrical strength of the pulse that should be delivered for defibrillation are almost invariably analyzed in terms of joules. Delivery of more than enough electrical energy for defibrillation has been associated with cardiac cell death, yet insufficient energy will not accomplish the desired defibrillation, resulting then in multiple attempts to defibrillate at ever higher energy levels.

Heretofore, recommendations for the "first attempt" defibrillation have been based on gross energy levels e.g., 100 joules. For example, U.S. Pat. No. 3,782,389 discloses a defibrillator that is computer controlled so that the energy actually delivered equals the predetermined energy sought to be delivered regardless of the patient load resistance. U.S. Pat. No. 3,862,639 adds the improvement of basing defibrillating current on the body weight of the patient.

The prior art approach to preselection of energy dose level for threshold defibrillation is believed to be suboptimal for several reasons. Body weight actually correlates poorly with threshold defibrillating requirements. For a given pulse duration, peak current is a better predictor of the defibrillation threshold than delivered energy. The inventor hereof has ascertained that defibrillating pulse levels based upon a specified level of peak amps per ohm of transthoracic resistance correlate well with threshold defibrillation requirements. Establishment of the defibrillation pulse on the basis of total electrical energy, as done by prior workers in the art, will not apply a consistent level of peak current (amperage) because transthoracic resistance, person to person, will vary within surprisingly large ranges.

The object of this invention is to provide a defibrillator method and apparatus for automatically providing a predetermined threshold level peak current according to the transthoracic resistance of each patient.

A further object of this invention is to provide a method and apparatus for determining and applying a threshold level of peak defibrillating current based on amps per ohm of transthoracic resistance.

Further objects of the invention and the advantages thereof will become apparent from the description which follows.

RATIONALE OF THE INVENTION

Although it has been customary in the defibrillator art to apply electrical energy as such, i.e., a pulse denominated in joules, some workers in the art have appreciated that delivered current is better than discharged energy as a measurement of a defibrillating threshold, as for example in U.S. Pat. No. 3,862,636, wherein the magnitude of the current delivered to the patient was varied in accordance with the body weight of the patient. In addition, other recent art has recognized that total energy may not be the most adequate electrical parameter to describe the dose for defibrillation, urging that the peak current level might be the best description of the energy needed to depolarize some critical mass of cells and achieve successful defibrillation, (in the instance of canine hearts at least). See, for example, Armayor et al. "Ventricular Defibrillation Threshholds with Capacitor Discharge", Med. & Biol. Eng. and Comput. 1979, Vol. 17, pp. 435–442. Note is made also of Kerber et al., "Advanced Prediction of Transthoracic Impedance in Human Defibrillation and Cardioversion: Importance of Impedance in Determining the Success of Low Energy Shocks", Circulation, Vol. 70, No. 2, pp. 303–308, 1984 (a report believed to describe research which may have been carried out subsequent to the invention hereof).

The gist of the above-noted art is that the need exists for identifying patients with such high thoracic resistance that application of relatively low energy, e.g., 100 joules, defibrillation shock levels are unlikely of success. The inventor hereof believes that such an approach is too gross, and that a superior approach would be to ascertain a threshold level of peak current which should be according to the requirements of each patient, and then apply whatever electrical energy will result in the desired level of peak current. Associating a resistance measuring system with the defibrillator circuitry and controlling the electrical shock energy administered by the defibrillator according to measured transthoracic resistance can provide a predetermined level of peak defibrillation current. Such has been done in the practice of this invention.

BRIEF STATEMENT OF THE INVENTION

Briefly stated, the defibrillator of this invention automatically determines transthoracic resistance, and then uses the thus-obtained resistance to calculate the threshold level of peak current required to effect defibrillation whereupon the defibrillator delivers that peak current.

After the defibrillating electrodes are in place, on a patient's chest, a low amplitude, sinusoidal pulse is transmitted through the electrodes. A microprocessor is used to calculate the transthoracic resistance in order that a preprogrammed, predetermined value of peak amperage per measured ohm of transthoracic resistance may be delivered to this subject by the defibrillator. The extreme rapidity of electrical measurements, and the rapid response of electrical circuits to control signals are advantageous, since ventricular fibrillation is of life threatening urgency and brooks no delay.

The signal indicative of the peak defibrillation current to be applied to the patient is used in the defibrillator circuitry to control the charge applied to the capacitor of the defibrillator, so that upon discharge of the capacitor, the calculated level of peak current desired for defibrillation will result.

Electrical components and circuitry known to the arts may be employed in practice of the invention. For example, in practice of the invention, standard microprocessors may be adapted to: calculate transthoracic resistance from delivered peak exploration current and the electrode-to-electrode voltage developed responsive thereto; multiply a preprogrammed amperage per ohm of transthoracic resistance by the calculated ohms of transthoracic resistance; and generate an appropriate output signal for controlling capacitor of the defibrillator so as to generate the desired level of the peak current for defibrillation.

Suitably, the microprocessor generates a digital signal for a visual readout, and for recording and, in addition, conversion to an analog form for direct control over the charge being placed on the capacitor of the defibrillator.

Desirably, the peak current subsequently delivered to the patient by the defibrillator, and the voltage of the capacitor or across the electrodes are digitized to generate signals which are fed into the microprocessor which, in turn, computes the transthoracic resistance encountered by the defibrillation pulse. The microprocessor then provides appropriate signals for visual readout and recording. For future defibrillation of the same and other patients, it is important to know the degree to which the level of peak current actually delivered by the defibrillator pulse relates to the previously calculated peak current level and how transthoracic resistance during defibrillation relates to resistance measured by the low amplitude exploration current. Given sufficient experiences, a virtually exact predicatability for delivered peak current should result, since appropriate adjustments can be made in the multiplication factor(s) programmed into the microprocessor.

DISCUSSION OF THE INVENTION

Mention has been made in that defibrillation art has concerned itself with measurement of thoracic resistance and, as might be expected, some suggestions heretofore made to the art are capable of use in practice of this invention, over and above the particular mode hereinafter described. For example, reference is made to "Determining Transthoracic Impedance, Delivered Energy, and Peak Current During Defibrillation Episodes" by Jones et al. in Medical Instrumentation, Vol. 15, No. 6, November–December 1981, pp. 380–382, and, of course, to Kerber et al. supra, as well as Armayor et al. supra.

Important to the practice of this invention is, of course, a consonance of the transthoracic resistance as measured by the low amplitude exploration pulse to the transthoracic resistance under defibrillation pulse circumstances. In this connection, it is noted that Kerber et al. reported that their predicted resistance correlated very well with defibrillation pulse resistance, and such correlation is expected to result when practice of this invention advances from the animal model results obtained in the genesis of this invention, (only such being available as of the date hereof) to widespread employment for defibrillation of humans.

It is noteworthy that in the relatively few human patients on which resistance measurements have been made by the inventor hereof (20 patients), the same relatively wide variation in transthoracic resistance person-to-person heretofore reported in the literature has been found to exist. The mean transthoracic human resistance as $72\pm21$ ohms, with the actual measured values being from 33 to 108 ohms. No linear correlation was found between transthoracic resistance and body weight, chest circumference, internal thoracic diameter or chest wall thickness. The transthoracic resistance in humans was found to be predominantly resistive, and not predictable from physical dimensions or body weight.

Through practice of this invention, the physician may apply a defibrillating shock which should be adequate without being excessive, i.e., be close to the threshold. Practice of this invention will automatically identify these patients at the extremes of the 33–108 ohm range of transthoracic resistance for whom the 100 joule defibrillator shock may be either far too low or excessively high and automatically will cause the defibrillator to apply a defibrillator shock that delivers a level of peak current more appropriate to the patient.

Comparative studies made on canines found that peak amperage per ohm of transthoracic resistance is a more accurate predictor of threshold defibrillating current than peak amperage per unit of body weight or per unit of heart weight. It has been found also that the transthoracic load of humans is apparently frequency insensitive, remaining constant throughout the frequency spectrum. Further, voltage and current in the defibrillating pulse were virtually in phase throughout all frequencies, with the percent of total energy delivered to 20 patients being $96\pm2\%$ resistive energy and $4\pm2\%$ reactive energy (Mean$\pm$Standard deviation).

Since transthoracic load is, therefore, predominantly resistive, the inventor has used the term "resistance" throughout this discussion when referring to the transthoracic load.

These findings have led to the conceptual framework for practice of this invention, which involves prospectively determining the transthoracic resistance of each patient by application of a low energy, high frequency pulse; then calculating a corresponding level of peak defibrillating current for each patient; thereafter automatically charging the defibrillator capacitor to the voltage level sufficient for delivery of the calculated level of peak current transthoracically on discharge; and automatically discharging the capacitor and defibrillating upon attaining such voltage level. All of these steps—from measurement through discharge—are performed with the electrodes on the patient.

Additionally, the voltage across the discharge capacitor of the defibrillator, and the peak current supplied by discharge thereof, may be measured so as to compute and display the transthoracic resistance for the defibrillation energy applied to the patient.

As pointed out by Jones et al., supra, knowledge of the internal circuit parameters peculiar to each defibrillator mode enables normalizing of the peak discharge current so that it is expressable as only a function of transthoracic resistance or resistance. Although not specifically included in the following description of the exemplary embodiment of this invention, normalization for circuit components (internal resistance) in the defibrillator is contemplated, including normalization for add-on internal circuit parameters such as those of the current sensing transformers; and the method and apparatus of the instant invention should be considered as inclusive of performing such normalization whenever desirable. The details of normalization described by Jones et al. supra are incorporated by reference herein as exemplary modes of normalization contemplated herein.

BRIEF DESCRIPTION OF THE DRAWINGS

For further understanding of this invention, reference is made to the attached drawing wherein.

DETAILED DESCRIPTION OF THE INVENTION

Figure 1:
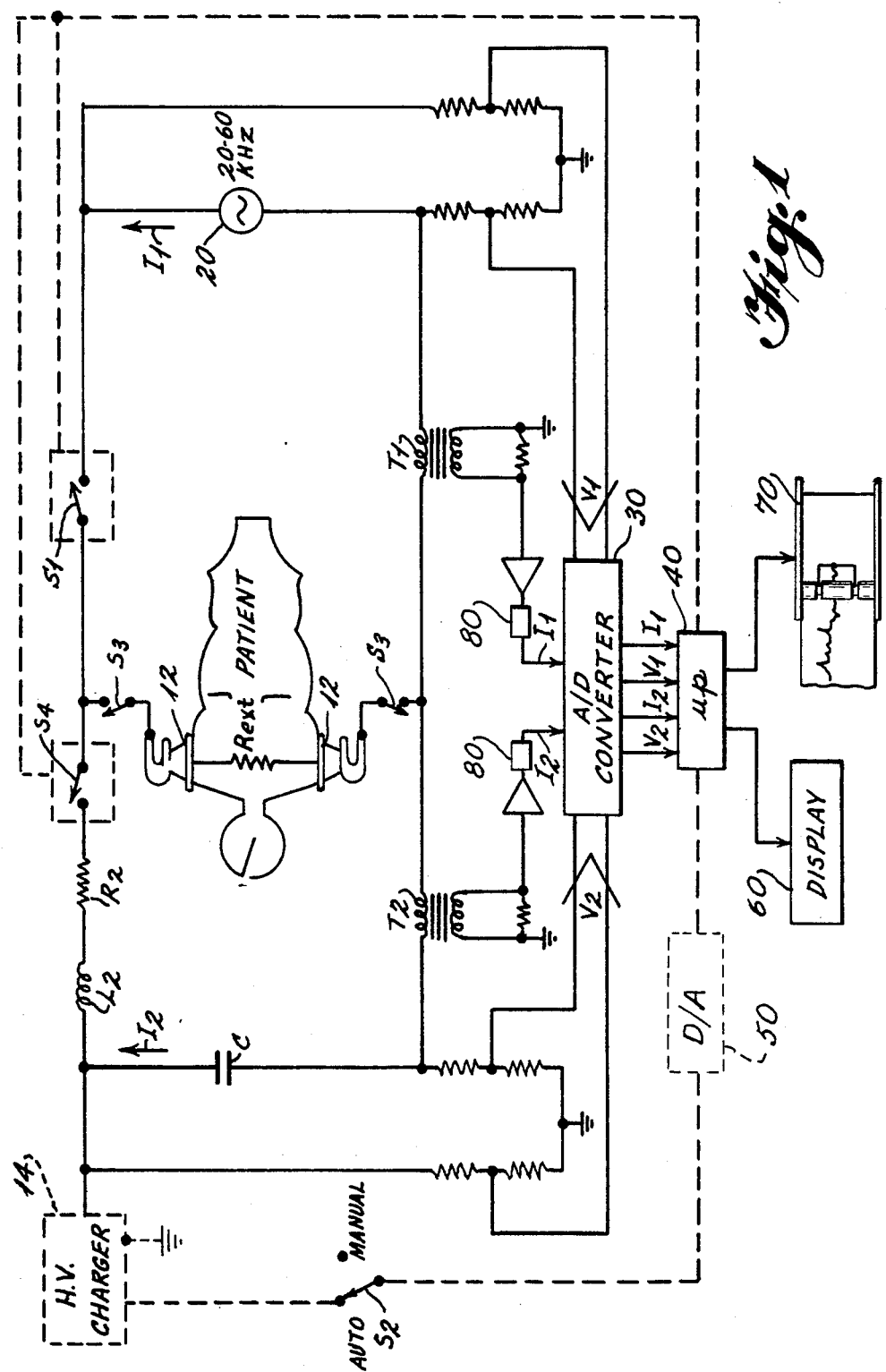
FIG. 1 is a schematic illustration of the invention and the use thereof.

As may be seen in FIG. 1, a conventional defibrillator includes hand-held electrode paddles 12 having switches $S_3$ which must be simultaneously closed in order to apply a defibrillation energy pulse transthoracically to the patient whose heart is in ventricular fibrillation. Closing of switches $S_3$ allows discharge of capacitor C and flow of defibrillating current $I_2$ through a circuit including the transthoracic resistance $R_{ext}$ of the patient. $L_2$ and $R_2$, respectively, represent the internal inductance and resistance parameters of the defibrillator. Additionally, the standard defibrillator includes a circuit for charging capacitor C, such indicated as high voltage charging circuit 14 in FIG. 1. FIG. 1 also discloses a current sensing transformer $T_2$ and an appropriate voltage divider so that the transthoracic resistance $R_{ext}$ may be computed as the quotient of the voltage $V_2$ across capacitor C divided by the peak defibrillating current $I_2$. As may be seen in FIG. 1, A/D convertor 30 and microprocessor 40 are used to facilitate calculation of transthoracic resistance during such defibrillation, much as suggested by Jones et al. supra.

According to practice of the invention, defibrillating current $I_2$ applied via paddles 12 is controlled according to the transthoracic resistance of each individual patient prior to performing defibrillation. A low amplitude (approximately 0.1 milliamp) constant current generator 20 provides a pulse of current at some fixed frequency in the range of 20/60 kHz, as an exploration current $I_1$ passed through paddles 12 via the patient's thorax prior to discharge of capacitor C. A response voltage $V_1$ is developed across paddles 12 appropriately proportional to the product of the transthoracic resistance $R_{ext}$ and the applied current $I_1$. Sensing current $I_1$ via transformer $T_1$ and measuring the response voltage $V_1$, allows a calculated transthoracic resistance $R_{ext\,1}$ to be obtained by passing the sensed current and voltage through A/D convertor 30 then to a microprocessor 40 in which the calculation is performed. Since transthoracic load is predominantly resistive (e.g., 96±2% resistive, compared to 4±2% reactive), it may be appreciated that the computed or calculated transthoracic resistance $R_{ext\,1}$ may then be used to compute a peak level of defibrillation current particular to the transthoracic resistance of each individual.

Just as 100 joules has been used heretofore as an experience—determined energy level for initial defibrillator shock, about 0.9 amperage per ohm of resistance value has been preselected in practice of this invention for the multiplication factor used to establish the peak level of defibrillation current. This value is based upon limited human patient experience and some change up or down therein may be required with increased human patient experience. As a practical matter, a value of 100% or so above the estimated threshhold peak current is believed to be acceptable for medical practice defibrillation, which would allow the factor to be up to about 2 Amp/ohm. The range of about 0.5-2 Amp/ohm is contemplated.

The concept of delivering a peak level of defibrillating current per ohm of transthoracic resistance is important to practice of this invention. Analysis of the data available to the inventor hereof has indicated that threshold level correlates with transthoracic resistance, the greater the resistance, the higher the threshold level. Thus, for patients of high transthoracic resistance, defibrillating with 100 joules may apply too low a level of peak defibrillating current (since amperage is inversely proportional to resistance) by reason of the high resistance. Application of some fixed level of peak current to all patients would be an improvement for eliminating current variation patient to patient, but is likely to fall short of the threshold needs for defibrillating high resistance patients, yet may damage the myocardium of patients with low transthoracic resistance. Proportioning current according to body weight, as has been suggested in the art, also can encounter failure to defibrillate or damage the myocardium because transthoracic resistance does not correlate well to body weight. To repeat, the conversion factor for establishing the calculated level of peak defibrillation current is an amperes of current per ohm of (calculated) transthoracic resistance conversion factor, which is to say, the higher the transthoracic resistance, the higher the peak current level required.

With an appropriate conversion factor, e.g., K=0.9 amps/ohm programmed into microprocessor 40, the appropriate level of peak defibrillation current $I_2$ is ascertained by multiplying together K and the calculated transthoracic resistance $R_{ext\,1}$.

With switch $S_2$ set to AUTO (for automatic) microprocessor 40 controls switches $S_1$ and $S_4$ and high voltage charger 14 such that, upon placing the paddles 12 upon the chest of the patient and depressing switches $S_3$, switch $S_1$ will be closed to apply the exploration current $I_1$ across the patient's chest. Prior to, during, or after measurement of transthoracic resistance, high voltage charger 14 commences to charge capacitor C. After calculating $R_{ext\,1}$, microprocessor 40, directly or indirectly, opens switch 1 and immediately controls the amount of voltage to which capacitor C is charged according to the calculated level required for peak defibrillating current $I_2$. Upon capacitor C being charged to a voltage sufficient to provide the calculated level of peak current $I_2$, microprocessor 40, directly or indirectly, will (automatically) close switch $S_4$ for consequent defibrillation of the patient. The operator may wish sometimes to apply standard defibrillator operation, i.e., setting of a particular energy level, e.g., in joules, for some particular patient and such is permitted; set switch $S_2$ to manual).

A display 60 and recording device 70 allow display and recordation of important defibrillation particulars such as: the transthoracic resistance $R_{ext\,1}$ calculated from the exploration current $I_1$; the transthoracic resistance $R_{ext\,2}$ computed during defibrillation of the patient; the calculated level of peak defibrillating current appropriate for the particular patient; and the measured level of peak defibrillating current $I_2$.

Figure 2:
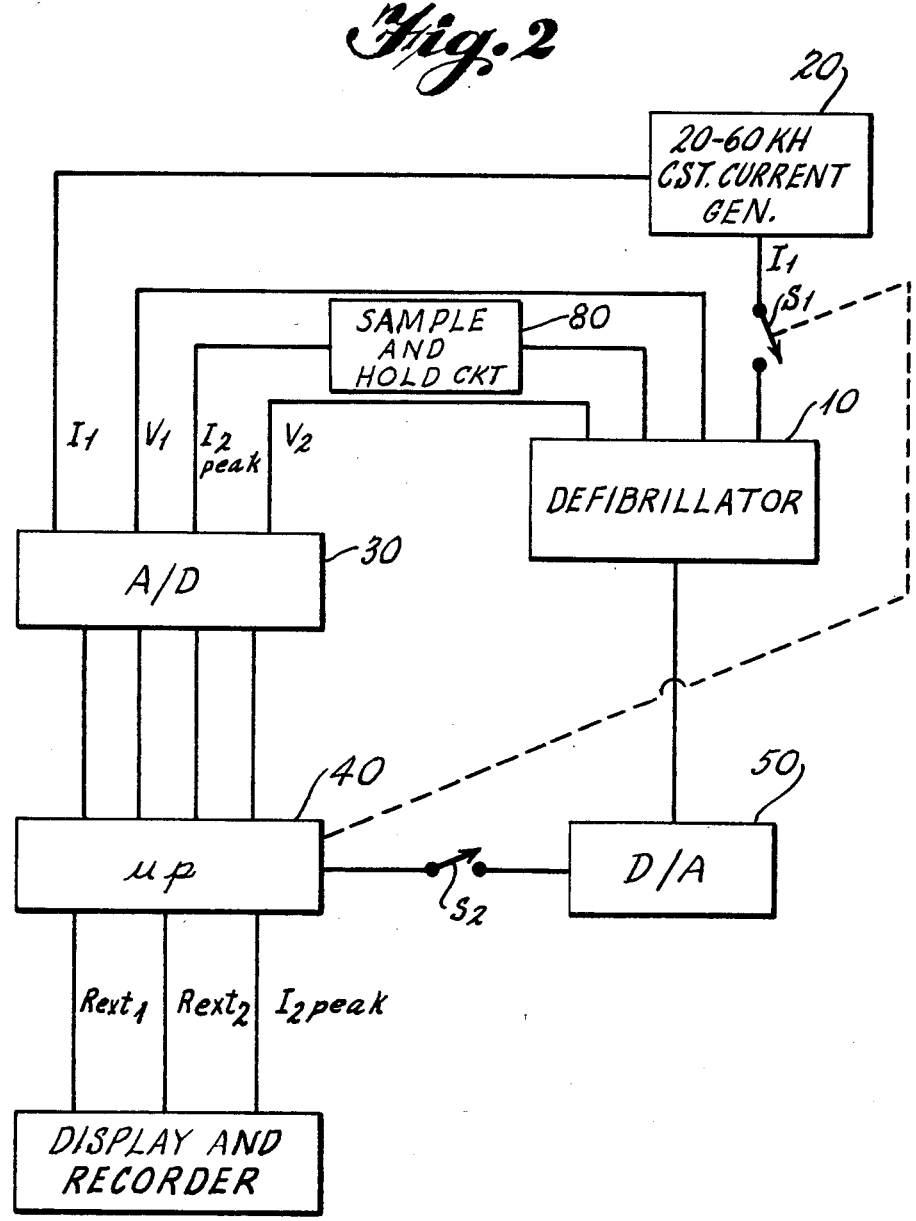
FIG. 2 is a block diagram illustrating a standard defibrillator and the add-on components utilized in practice of the instant invention.

FIG. 2 is a block diagram generally illustrating the add-on components used with the standard defibrillator 10 to practice of the present invention. Like numerals have been used for like parts in the drawings.

I claim:

1. A method of determining an optimum threshold level of peak defibrillation current to be applied to the chest of a particular patient by means of a defibrillator in order to correct ventricular fibrillation, and comprising the steps of:

(a) applying a low amplitude exploration current from electrodes forming part of said defibrillator to said chest and sensing voltage developed thereby across said electrodes;

(b) calculating transthoracic resistance from said exploration current and response voltage; and (c) multiplying said transthoracic resistance by an ampere per ohm factor, the resulting amperage being the level of peak current to be applied to the patient for defibrillation.

2. A method as in claim 1 wherein said factor is at least about 0.9 amperes per ohm of resistance.

3. A method as in claim 1 wherein a frequency of said exploration current is in the range of about 20–60 kHz.

4. A method of defibrillating a patient having ventricular fibrillation comprising the steps of:

(a) applying a low amplitude exploration current from electrodes forming part of a defibrillator to the chest of said patient and sensing voltage developed thereby across said electrodes;

(b) calculating transthoracic resistance from said exploration current and response voltage;

(c) multiplying said transthoracic resistance by an amperes per ohm factor;

(d) charging the defibrillator capacitor according to said resulting amperage to create the capacitor discharge voltage generative of said resulting amperage as the level of peak current; and (e) discharging said defibrillator capacitor and defibrillating.

5. A method as in claim 4 further comprising the steps of:

calculating transthoracic resistance from the peak defibrillating current and capacitor discharge voltage; and displaying the values of both transthoracic resistances and of the peak defibrillation current.

6. A method as in claim 4 wherein said factor is at least about 0.9 amperes per ohm of resistance.

7. An apparatus for determining an optimum threshold level of peak defibrillation current to be applied to the chest of a particular patient by means of a defibrillator in order to correct for ventricular fibrillation and comprising:

(a) means for applying a low amplitude exploration current from electrodes forming part of said defibrillator to said chest and sensing voltage developed thereby across said electrodes;

(b) means for calculating transthoracic resistance from said exploration current and response voltage; and (c) means for multiplying said transthoracic resistance by an ampere per ohm factor, the resulting amperage being the level of peak current to be applied to the patient for defibrillation.

8. An apparatus as in claim 7 wherein said factor is at least about 0.9 amperes per ohm of resistance.

9. An apparatus for defibrillating a patient having ventricular fibrillation comprising:

means for applying a low amplitude exploration current from electrodes forming part of a defibrillator to the chest of said patient and sensing voltage developed thereby across said electrodes;

means for calculating transthoracic resistance from said exploration current and response voltage;

means for multiplying said transthoracic resistance by an ampere per ohm factor, the resulting amperage being the level of defibrillation peak current applied to said chest via said electrodes during subsequent defibrillation; and defibrillator means adapted to apply an electrode voltage sufficient to provide said defibrillation peak current;

said defibrillator means further comprising a capacitor and a charging means therefor forming part of the defibrillator means, the capacitor charging means being controlled so as to charge the capacitor to the voltage which provides said level of defibrillation peak current.

10. An apparatus as in claim 9 further comprising:

means for calculating transthoracic resistance from the peak defibrillating current and said discharge voltage; and means for displaying the value of both transthoracic resistances and of the peak defibrillation current.

11. An apparatus as in claim 9 wherein said factor is at least about 0.9 amperes per ohm of resistance.

* * * * *